(12) United States Patent
Landwehr

(10) Patent No.: US 10,247,649 B2
(45) Date of Patent: Apr. 2, 2019

(54) SPINE TESTING DEVICE AS WELL AS MEASURING METHOD

(71) Applicant: Meik Andre Landwehr, Paderborn (DE)

(72) Inventor: Meik Andre Landwehr, Paderborn (DE)

( * ) Notice: Subject to any disclaimer, the term of this patent is extended or adjusted under 35 U.S.C. 154(b) by 368 days.

(21) Appl. No.: 15/078,215

(22) Filed: Mar. 23, 2016

(65) Prior Publication Data

US 2017/0176307 A1 Jun. 22, 2017

(30) Foreign Application Priority Data

Dec. 17, 2015 (DE) .......................... 10 2015 122 052

(51) Int. Cl.

| | |
|---|---|
| *G01L 1/00* | (2006.01) |
| *G01L 3/00* | (2006.01) |
| *G01L 5/00* | (2006.01) |
| *G01N 3/20* | (2006.01) |
| *F42B 35/00* | (2006.01) |
| *F41B 5/14* | (2006.01) |

(52) U.S. Cl.
CPC .............. *G01N 3/20* (2013.01); *F41B 5/14* (2013.01); *F41B 5/148* (2013.01); *F42B 35/00* (2013.01)

(58) Field of Classification Search
CPC .... G01N 3/00; G01N 3/20; G01N 2203/0023; F41B 5/14; F41B 5/148
See application file for complete search history.

(56) References Cited

U.S. PATENT DOCUMENTS

| | | | | | |
|---|---|---|---|---|---|
| 4,203,308 | A | * | 5/1980 | Davis ....................... | B21D 3/10 |
| | | | | | 72/31.03 |
| 7,788,982 | B2 | * | 9/2010 | Dee ........................... | G01N 3/04 |
| | | | | | 73/760 |
| 8,608,531 | B1 | * | 12/2013 | Huang .................. | B24B 41/067 |
| | | | | | 451/386 |
| 9,046,452 | B1 | * | 6/2015 | Huang ..................... | G01N 3/20 |
| 2012/0073383 | A1 | * | 3/2012 | You ........................... | G01N 3/20 |
| | | | | | 73/847 |

FOREIGN PATENT DOCUMENTS

DE         102009026989 A1    12/2010

* cited by examiner

*Primary Examiner* — Toan K Le
(74) *Attorney, Agent, or Firm* — Patent Central LLC; Stephen A. Pendorf

(57) ABSTRACT

A spine testing device having bearing supports located at a horizontal distance from one another in order to support opposite ends of an arrow, a measuring unit for determining a spine value of the arrow and a display unit for displaying the spine value. The bearing supports are equipped with a weighing device in order to measure a force emanating from the arrow. A stop is located in an area between the weighing devices at such a height that the arrow can be brought by a specified distance from a horizontal starting position into a bending position by exerting a force at a point of application of the same located between the ends of the arrow, in which bending position the application portion of the arrow lies in contact with the stop. The measuring unit includes an evaluation device having means for establishing a bending force acting on the arrow. The evaluation device includes a calculation formula with at least one reference value, so that the spine value of the arrow can be calculated by means of the calculation formula.

20 Claims, 2 Drawing Sheets

SPINE TESTING DEVICE AS WELL AS MEASURING METHOD

Figure 1:
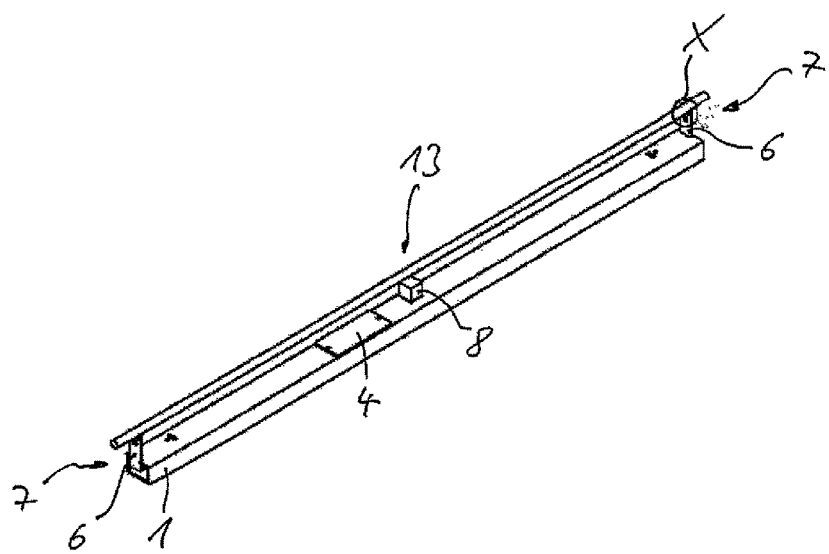

The invention relates to a spine testing device having bearing supports located at a horizontal distance from one another in order to support opposite ends of an arrow, having a measuring unit for determining a spine value of the arrow and having a display unit for displaying the spine value.

In addition, the invention relates to a method for determining a spine value for an arrow, wherein the arrow is positioned in a starting position with each of its opposite ends on a bearing support, the arrow is bent from the starting position into a bending position by grasping the same at a point of application located between the ends and the spine value of the arrow is determined after reaching the bending position.

A spine testing device which comprises a retaining unit with bearing supports located opposite one another for receiving an arrow is known from DE 10 2009 026 989 A1. A measuring unit for determining the spine value is provided in a central area. This measuring unit includes a weight which can be moved along a vertical rail and which bends the arrow at a point of application by means of a slider. The bending is effected by means of a force which is predetermined by a standard. For example, the AMO standard specifies that the arrow is deposited on bearing supports located at a distance of 26 inches from one another and is bent with a force of 2 pounds (908 g). The deflection caused by the bending or distance of the point of application between a horizontal starting position and a bending position of the arrow constitutes the spine value, wherein this distance is determined by a suitable measuring transducer and is then transmitted to a display unit for displaying the spine value. According to an alternative spine determination standard, namely the ASTM standard, the bearing supports are located at a distance of 28 inches. A value of 1.94 pounds (880 g) is applied to the central point of application of the arrow as the weight force. The disadvantage of the known spine testing device is that it is relatively expensive and yet tends to produce inaccurate measurement results.

The object of this invention is to indicate a spine testing device and a method for determining a spine value for an arrow so that, on the one hand, the measurement accuracy can be improved and, on the other hand, the component outlay can be reduced.

In order to achieve this object the invention in conjunction with the preamble of Claim 1 is characterized in that the bearing supports are equipped with a weighing device in order to measure a force emanating from the arrow, that a stop is located in an area between the weighing devices at such a height that the arrow can be brought by a specified distance from a horizontal starting position into a bending position by exerting a force at a point of application of the arrow located between the ends of the same, in which bending position the application portion of the arrow lies in contact with the stop, that the measuring unit comprises an evaluation device having means for establishing a bending force acting on the arrow and that the evaluation device comprises a calculation formula with at least one reference value, so that the spine value of the arrow can be calculated by means of the calculation formula.

According to the invention, a spine testing device is created which, on the one hand, is compact and light and, on the other hand, increases the measuring accuracy. In order to determine input variables, the spine testing device according to the invention only requires two weighing devices assigned to the bearing supports, by means of which forces can be measured. Interacting with an evaluation device, to which the input values (input variables) are supplied, the spine values of the arrow can be determined with reference to predetermined parameters and/or reference values. A stop limits the deflection and/or the bending of the arrow, wherein the measured values present in this position of the arrow are fed by the weighing device to the evaluation device, so that the spine value can be calculated by means of a predetermined calculation formula. The basic idea of the invention is to carry out a specified bending of the arrow, namely by moving a preferably central point of application on the arrow, in order to travel a specified distance up to the stop and to calculate the spine value from the determined input variables. Unlike the prior art, an arrow-dependent deflection is not effected by applying a constant force but, rather, a specified and constant deflection for all of the arrows which are to be examined, wherein the spine value for the respective arrows is calculated and/or determined, taking the different arrow-dependent force measurements as the basis. As a result, spine values of relatively stiff arrows can also be advantageously determined with a great deal of accuracy.

According to a preferred embodiment of the invention, a first force value determined by the weighing device in the starting position of the arrow, on the one hand, and a second force value determined by the same weighing device in the bending position of the arrow are supplied to the calculation formula as input values. The spine value can thus be calculated, together with the stored reference values.

According to a further development of the invention, the evaluation device comprises a micro-processor or a micro-controller, by means of which the spine value can be calculated.

According to a further development of the invention, the weighing device is configured as an electronic scale, so that the measured values can be supplied to the evaluation device in digital form for further processing.

According to a further development of the invention, the measuring unit includes a height measuring device, so that the straightness of arrows can be determined. An extension of the measuring values can advantageously be provided by this. In addition, the spine value of a crooked arrow can be established with just a single measurement. An averaged measurement of an arrow rotated by 180° is not necessary.

According to a further development of the invention, the bearing support comprises a U-shaped receptacle. The arrow is therefore advantageously securely held in a horizontal plane. The U-shaped receptacles are located collinearly to one another, so that a positioning of the arrow in a horizontal direction is guaranteed. In addition, the straight support surface results in a constant distance for different diameters of arrow.

According to a further development of the invention, the evaluation device and/or the display unit comprise(s) a digital interface for externally reading out and/or storing the measured values, in particular the spine values. The interface can be designed such that the measured values can be read out via Wi-Fi, Bluetooth or USB.

In order to achieve the object, the method according to the invention in conjunction with the pre-amble of Claim 10 is characterized in that the point of application of the arrow is moved by a specified distance from the starting position into the bending position of the arrow and that the spine value is determined by means of a calculation formula, wherein a first force determined in the starting position of the arrow at the ends of the same and a second force determined in the bending position at the end of the arrow are supplied to the calculation formula as input variables.

The measuring method according to the invention advantageously makes it possible to simply and precisely determine a spine value for different arrows. A weighing device and a stop are used to record measurement values, so that the measurement can be carried out without the presence of moving parts. According to the invention, a central point of application of the arrow is moved by a specified distance, wherein the forces emanating from the arrow in the horizontal starting position of the same and in the bending position of the same are used as input variables. The spine value of the arrow can then be calculated and, if necessary, displayed by means of a predetermined calculation formula which preferably takes account of a parameter which is fixed according to a standard and/or reference values. The spine value is therefore measured indirectly, as it is not the bending deflection of the arrow directly which is determined, but simply the force conditions in a predetermined bending position and then the spine value is calculated from this. According to the invention, only the ends of arrows are therefore weighed. The measurement outlay is advantageously low and the measuring accuracy is relatively high. The weight of the arrow is established and displayed in a single operation.

According to a further development of the method according to the invention, the bending deflection of the arrow takes place manually. As a result, the measuring outlay can be advantageously substantially reduced. The fact that the point of application of the arrow only has to be pressed against a stop means that the risk of a measuring error is relatively low.

Figure 2:
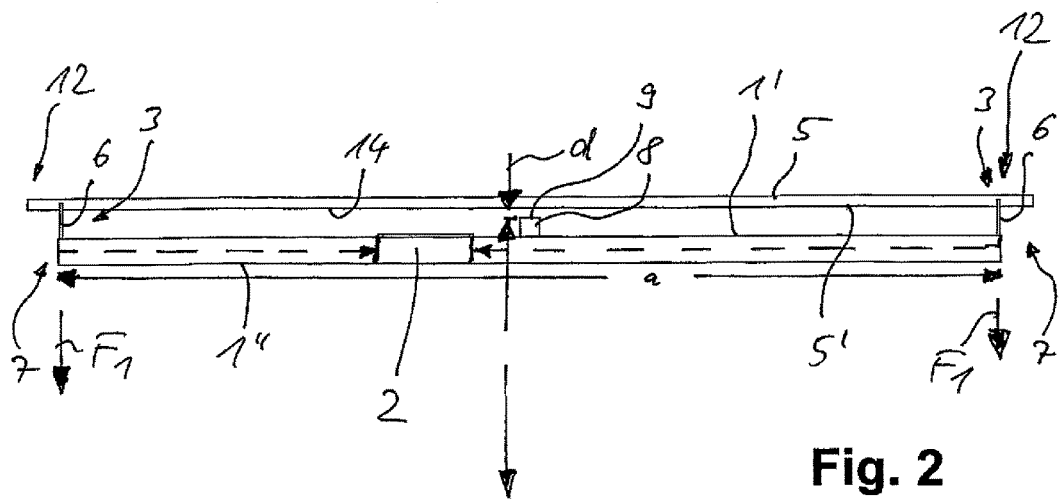
Figure 3:
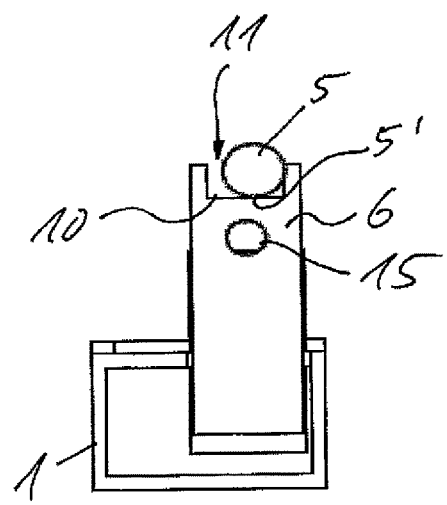
Figure 4:
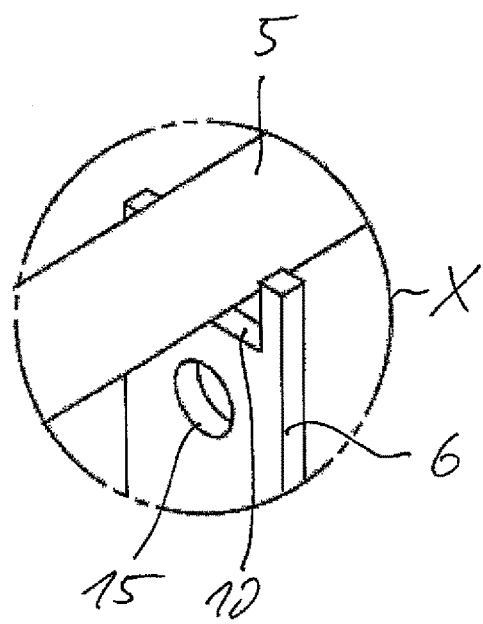

One embodiment example of the invention will be explained below using the drawings, wherein:

FIG. 1 shows a perspective view of a spine testing device having an arrow mounted in a starting position, FIG. 2 shows a side view of the spine testing device according to FIG. 1, FIG. 3 shows a front view of the spine testing device and FIG. 4 shows an enlarged detail X in FIG. 1.

A spine testing device comprises a tubular housing 1 in which an evaluation device 2 of a measuring unit 3 and a display unit 4 are substantially integrated.

The measuring unit 3 for determining a spine value of the arrow 5, which is deposited on bearing supports 6 which are located at a distance a from one another in an illustrated starting position, comprises weighing devices 7 integrated in each case in a bearing support 6, and a stop 8 in a central area of the housing 1 elevated from the same for measuring purposes. The stop 8 comprises an upper stop face 9 which is located at a height from a top 1' of the housing 1. The height of the stop 8 is dimensioned such that support edges 10 of the bearing supports 6 and/or a bottom 5' of the arrow 5 have a predetermined vertical distance d from the stop face 9.

The bearing supports 6 each have a U-shaped receptacle 11 for ends 12 of the arrow 5, so that the arrow is located horizontally in a starting position. The U-shaped receptacles 11 are located collinearly to one another, so that the arrow 5 rests in such a manner that it is displaceable along its longitudinal axis. The U-shaped receptacles 11 and/or the support edges 10 of the same project at an equal distance from the top 1' of the housing 1 and/or a bottom 1" of the housing 1. This ensures that the arrow 5 is mounted horizontally in the starting position. The bottom 1" of the housing 1 is preferably configured to be level.

The spine value of the arrow 5 is measured in a two-step method. In a first step, in which the arrow 5 has been deposited on the bearing supports 6, without a force acting on it, a weight force $F_1$ is measured by means of the weighing device 7 and is fed to the evaluation device 2 as an input variable. The weighing device 7 is preferably configured as a digital scale, so that the measurement value can be fed, without being converted, directly to the evaluation device 2 which is configured with a microprocessor or a micro-controller. The arrow 5 is located in a horizontal starting position in this first step of the measuring method.

After the weight force $F_1$ of the arrow 5 has been measured, which can be communicated by optical and/or acoustic signaling which is not shown, the arrow 5 is bent manually. To this end, for example, a finger of a person grasps the arrow 5 at a point of application 13 located in a central portion, said point of application being located perpendicularly to the stop 8. The arrow 5 is bent in the direction of the stop 8, grasping and/or seizing it at the point of application 13, until the arrow 5 has reached a bending position, in which a bottom 14 of the arrow 5 facing the stop 8, said bottom being located opposite the point of application 13, lies in contact with the sloping surface 9 of the stop 8. A second force value $F_2$ is recorded in this bending position of the arrow 5 by means of the weighing device 7. The spine value can be determined from the determined values $F_1$ and $F_2$ in conjunction with predetermined reference values stored in the evaluation device 2 by applying a calculation formula.

A predetermined bending force $F_{REF}$ and a reference spine value $d_{REF}$ are stored as reference values in a memory of the evaluation device 2. The bending force $F_{Biege}$ acting on the arrow 5 is determined from the difference determined between the second force $F_2$ in the bending position of the arrow 5 and the first force $F_1$ in the starting position of the arrow 5. The calculation formula provides for the following relationship:

$$d_{Spine}/d_{REF} = F_{REF}/F_{Biege}.$$

The spine value $d_{Spine}$ of the arrow 5 can be determined from this, by generating a relationship of the reference bending value $F_{REF}$ with the determined bending force $F_{Biege}$, wherein this quotient is multiplied by the spine reference value $d_{REF}$. The determined spine value $d_{Spine}$ of the arrow 5 is then shown in the display unit 4.

The arrow 5 can then be released, in order to carry out an additional control measurement following twisting of the arrow 5 at an angle about its longitudinal axis. Variations of the spine value can be determined during this.

The measuring process can be repeated after rotating the arrow by 180°, wherein the evaluation device calculates and/or outputs an average of the calculated spine values. This produces a spine value which compensates for crooked arrows.

It is noted that the bearing distance a as well as the distance d between the arrow 5 and the sloping surface 9 are also included as parameters in the calculation of the spine value $d_{Spine}$. The bearing distance a preferably coincides with the distance of 26 inches in accordance with the AMO standard or 28 inches in accordance with the ASTM standard. Alternatively, a different distance can also be selected, whereby the bending force $F_{Biege}$ must then be converted to the distance according to the standard.

The spine testing device and/or the display unit 4 preferably comprise(s) means so that the spine value $d_{Spine}$ can be displayed according to different standards.

The specified distance d and/or the bending path d of the arrow 5 should be dimensioned such that the maximum weight of a relatively rigid arrow 5 detected by the weighing devices 7 is not exceeded. At a bearing distance of 28 inches, this produces a specified distance d of approx. 8 mm.

The spine value of relatively crooked arrows is determined by means of a double measurement, wherein the arrow is rotated by 180°. The spine value is then generated by the average of the determined spine values.

The deviation in the straightness of the arrow 5 can additionally be measured by means of a height measuring device and then displayed by means of the display unit 4. The determined height measurement is taken into account in the calculation of the spine value, so that the spine value can also be established in the case of crooked arrows with only a single measurement. In addition, the exact establishment of the spine value is hereby also guaranteed for non-cylindrically formed arrows.

The evaluation device 2 and/or the display unit 4 can comprise an interface for externally reading out and/or storing the determined spine values $d_{Spine}$. The stop 8 is preferably located centrally between the bearing supports 6 and/or the weighing devices 7.

According to an alternative embodiment of the invention which is not shown, the arrow 5 can also be deflected up to the stop 8 by means of a mechanically and/or electrically driven slider.

In order to store or hold tips of the arrow 5, the bearing supports 6 comprise receptacle holes 15 in which the tip of the arrow 5 can be stored. These can be used to measure the weight of the arrow tips.

It is noted that two weighing devices 7 are sufficient to measure the force values.

Alternatively, only a single weighing device 7 can be provided as well. This single weighing device 7 can be integrated in a first front area of the housing 1 in the bearing support 6. In a second front area of the housing 1, the bearing support 6 is merely provided with a bearing surface or with a bearing edge 10 without a weighing function. This can also be used to measure the spine value, but not the weight of the arrow 5.

If necessary, more than two weighing devices 7 can also be provided. The distance of the weighing devices 7 from one another is smaller in this case.

The invention claimed is:

1. A spine testing device having
    first and second bearing supports (6) located at a horizontal distance (a) from one another in order to support opposite ends (12) of an arrow (5),
    a measuring unit (3) for determining a spine value ($d_{Spine}$) of the arrow (5) and
    a display unit (4) for displaying the spine value ($d_{Spine}$), wherein:
        at least one of said first and second bearing supports (6) is equipped with a measuring device (7) in order to measure a force ($F_1$, $F_2$) emanating from the arrow (5),
        a stop (8) is located in an area between the first and second bearing supports, at such a height that the arrow (5) can be moved a specified distance (d) from a horizontal starting position into a bending position by exerting a force at a point of application (13) located between the first and second bearing supports (6), in which bending position the arrow (5) lies in contact with the stop (8),
        the measuring unit (3) comprises an evaluation device (2) having means for establishing a bending force ($F_{Biege}$) acting on the arrow (5) and the evaluation device (2) comprises a calculation formula with at least one reference value, so that the spine value ($d_{Spine}$) of the arrow (5) can be calculated by means of the calculation formula.

2. The spine testing device according to claim 1, wherein a first force value ($F_1$) of the arrow (5) located in the starting position determined by the at least one weighing device (7) and a second force value ($F_2$) of the arrow (5) located in the bending position can be supplied to the calculation formula of the evaluation device (2) as input values.

3. The spine testing device according to claim 2, wherein the calculation formula generates a difference between the first force value ($F_1$) and the second force value ($F_2$) in order to determine the bending force ($F_{Biege}$) acting on the arrow (5) in the bending position, on the one hand, and generates a relationship of the reference values and the determined bending force ($F_{Biege}$) in order to calculate the spine value ($d_{Spine}$).

4. The spine testing device according to claim 1, wherein a reference bending force ($F_{REF}$) and a reference distance ($d_{REF}$) are stored as reference values in a memory of the evaluation device (2).

5. The spine testing device according to claim 1, wherein the evaluation device (2) includes a microprocessor or a micro-controller, in which the calculation formula is implemented.

6. The spine testing device according to claim 1, wherein the measuring device (7) is an electronic scale which supplies the measured value to the evaluation device (2) as a digital input value.

7. The spine testing device according to claim 1, wherein the measuring unit (3) has a height measuring device for establishing the straightness of the arrow (5).

8. The spine testing device according to claim 1, wherein the bearing support (6) is a U-shaped receptacle (11).

9. The spine testing device according to claim 1, wherein the evaluation device (2) and/or the display unit (4) comprise(s) an interface for externally reading out and/or storing the spine values ($d_{Spine}$).

10. The spine testing device according to claim 1, wherein the evaluation device (2) comprises means for converting the spine value ($d_{Spine}$) according to different standards.

11. The spine testing device according to claim 1, wherein the spine of the arrow has a constant diameter along its length.

12. A method for determining a spine value for an arrow (5), said method comprising:
    positioning the arrow (5) in a horizontal starting position with arrow opposite first and second ends (12) on first and second bearing supports (6) located at a horizontal distance (a) from one another,
    bending the arrow (5) from the horizontal starting position into a bending position by grasping the arrow (5) at a point of application (13) located between the ends (12) and applying a bending force to move the point of application (13) a specified distance (d) from the horizontal position into the bending position of the arrow (5), and
    determining the spine value ($d_{Spine}$) of the arrow (5) after reaching the bending position, by means of a calculation formula, wherein a first force ($F_1$) is determined at the ends (12) of the arrow with the arrow (5) in the horizontal starting position, a second force ($F_2$) is determined at the ends (12) of the arrow with the arrow (5) in the bending position, and the determined first force ($F_1$) and second force ($F_2$) are supplied to the calculation formula as input variables.

13. The method according to claim 12, wherein the point of application (13) of the arrow (5) is moved manually from the horizontal starting position into the bending position of the arrow (5).

14. The method according to claim 12, wherein the point of application (13) of the arrow (5) is moved vertically from the horizontal starting position into the bending position of the arrow (5).

15. The method according to claim 12, wherein a predetermined bending force $F_{REF}$ and a reference spine value $d_{REF}$ are stored as reference values in a memory of the evaluation device (2), wherein the bending force ($F_{Biege}$) acting on the arrow (5) is determined from the difference between the determined second force ($F_2$) in the bending position of the arrow (5) and the determined first force ($F_1$) in the horizontal starting position of the arrow (5).

16. The method according to claim 15, wherein he calculation formula provides for the following relationship:

$$d_{Spine}/d_{REF}=F_{REF}/F_{Biege}.$$

17. The method according to claim 16, further comprising determining the spine value $d_{Spine}$ of the arrow (5) by generating a relationship of the reference bending value $F_{REF}$ with the determined bending force $F_{Biege}$, and multiplying this quotient by the spine reference value $d_{REF}$.

18. The method according to claim 17, further comprising displaying the determined spine value $d_{Spine}$ of the arrow (5) in the display unit (4).

19. A spine testing device having
first and second bearing supports (6) located at a-horizontal distance (a) from one another and supporting opposite ends (12) of a spine of an arrow (5), said spine having a top and a bottom (5'), wherein at least one of said first and second bearing supports (6) is equipped with a measuring device (7) in order to measure a force ($F_1$, $F_2$) applied to the arrow (5) at a point of application (13) located between the first and second bearing supports (6),
a stop (8) located centrally in an area between the first and second bearing supports, below the arrow (5) at such a height that the arrow (5) can be moved vertically a specified distance (d) from a horizontal starting position into a bending position by exerting a force at a point of application (13), in which bending position the arrow (5) lies in contact with the stop (8),
a measuring unit (3) for determining a spine value ($d_{Spine}$) of the arrow (5) and
a display unit (4) for displaying the spine value ($d_{Spine}$),
wherein the measuring unit (3) comprises an evaluation device (2) having means for establishing a bending force ($F_{Biege}$) acting on the arrow (5) and the evaluation device (2) comprises a calculation formula with at least one reference value, so that the spine value ($d_{Spine}$) of the arrow (5) can be calculated by means of the calculation formula.

20. The spine testing device according to claim 19, wherein the spine of the arrow has a constant diameter along its length.

* * * * *